United States Patent [19]  [11]  4,404,040
Wang  [45]  Sep. 13, 1983

[54] SHORT CHAIN FATTY ACID SANITIZING COMPOSITION AND METHODS

[75] Inventor: Yueh Wang, Apple Valley, Minn.

[73] Assignee: Economics Laboratory, Inc., St. Paul, Minn.

[21] Appl. No.: 279,442

[22] Filed: Jul. 1, 1981

[51] Int. Cl.³ .......................... B08B 9/00; C11D 3/48; C11D 7/08; A61L 2/00

[52] U.S. Cl. .................................... 134/22.14; 134/30; 422/28; 252/106; 252/108; 252/135; 252/142; 252/174.16; 252/DIG. 14; 252/DIG. 17; 252/363.5

[58] Field of Search ............... 252/106, 108, 135, 142, 252/174.16, 363.4, DIG. 17, DIG. 14; 134/22.14, 30; 422/28

[56] References Cited

U.S. PATENT DOCUMENTS

| | | | |
|---|---|---|---|
| 3,083,166 | 3/1963 | Harding | 252/142 |
| 3,223,643 | 12/1965 | Law | 252/106 |
| 3,223,644 | 12/1965 | Law | 252/106 |
| 3,650,964 | 3/1972 | Sedliar et al. | 252/106 |
| 3,650,965 | 3/1974 | Cantor et al. | 252/106 |
| 3,824,190 | 7/1974 | Winicus et al. | 252/106 |
| 3,829,506 | 8/1974 | Schmolka et al. | 252/106 X |
| 3,867,300 | 2/1975 | Karabines et al. | 252/106 |
| 3,969,258 | 7/1976 | Carandang et al. | 252/106 |
| 3,975,280 | 8/1976 | Hachmann et al. | 252/106 X |
| 4,002,775 | 1/1977 | Kabara | 426/532 |

FOREIGN PATENT DOCUMENTS

| | | | |
|---|---|---|---|
| 2401062 | 7/1974 | Fed. Rep. of Germany | 252/142 |
| 2058823 | 4/1981 | United Kingdom | 252/142 |

Primary Examiner—Michael R. Lusignan
Attorney, Agent, or Firm—Merchant, Gould, Smith, Edell, Welter & Schmidt

[57] ABSTRACT

Sanitizing concentrate and "use" compositions comprising aliphatic, short chain fatty acid (i.e., $C_6$–$C_{14}$ fatty acid), hydrotrope or solubilizer for the fatty acid, hydrotrope-compatible acid so that the concentrate, when diluted with a major amount of water provides a use solution having a pH in the range of 2.0 to 5.0. Sanitizing of substantially fixed, "in-place" processing lines in dairies, breweries and other food processing operations is a particular utility of this invention.

26 Claims, No Drawings

SHORT CHAIN FATTY ACID SANITIZING COMPOSITION AND METHODS

This invention relates to cleaning or sanitizing compositions of matter. More particularly, this invention relates to short chain fatty acid sanitizing compositions which are low-foaming, biodegradable, and advantageously biostatic or biocidal. The compositions of the present invention are useful to sanitize hard surfaces (e.g., warewashing) and are particularly useful in the dairy and beverage industry for sanitizing substantially fixed, processing facilities such as pipelines and continuously operating homogenation or pasteurization apparatus. The instant compositions also have been found to be useful in low temperature (e.g., 100° F. (37° C.) to 120° F. (50° C.) or less) laundry applications.

It is well known that numerous classes of chemical compounds exhibit varying degrees of anti-microbial activity. The patent literature contains many disclosures relating generally to anti-microbial or sanitizing compositions. For example, U.S. Pat. No. 3,969,258 to Carandang et al. teaches a sanitizer composition comprising (a) a normally high foaming anionic surfactant, (b) a strong acid providing low pH in the range of 1.8 to 2.5, (c) $C_8$–$C_{18}$ aliphatic alcohol or $C_9$–$C_{12}$-alkyl substituted phenol or a mixture thereof to suppress the foaming tendencies of the anionic surfactant, and (d) polyvalent metal compound. U.S. Pat. No. 4,002,775 to Kabara teaches the unexpected, biocidal effectiveness of the mono-esters of twelve carbon atom (i.e. lauric acid), aliphatic fatty acids and polyols generally having fewer than eight carbon atoms such as glycols, glycerol, and polyhydroxy cyclic species such as sucrose.

Further, U.S. Pat. No. 3,867,300 to Karabinos et al teaches the surprising bactericidal activity of relatively concentrated (i.e., 5 to 15 percent) $C_8$–$C_{11}$ aliphatic monocarboxylic acid, the composition generally having a pH approaching that of skin (e.g., approximately 7) and further containing a nonionic or anionic surfactant. U.S. Pat. No. 3,650,965 to Cantor et al describes a low foam detergent composition consisting of two specific classes of nonionic surfactants, $C_{8-18}$ aliphatic monocarboxylic acid or alcohol defoamers, and mineral acid when carboxylic acids are selected. Sanitizing capabilities of the Cantor et al composition are provided by adding iodine. Cantor et al do not recognize nor appreciate the sanitizing capability of short chain aliphatic carboxylic acids. Nor do Cantor et al recognize that nonionic surfactants tend to detract from the biocidal or biostatic efficacy of the short chain fatty acids described herein.

Other sanitizer composition patents thought to be representative of the art include U.S. Pat. Nos. 3,650,964, 3,829,506, 3,223,643, 3,223,644 and 3,824,190. None of these patents disclose or suggest the present sanitizing composition which has the unique advantages of being biocidal or biostatic (hereafter "antimicrobial") even at relatively low use concentrations, non-toxic, biodegradable, surface active, preferably low-foaming with good shelf stability.

Briefly, in one aspect, the present invention is a concentrate which is capable of being diluted with a major amount of water to form a generally low-foaming, antimicrobial (e.g., antibacterial) sanitizing "use" solution, the concentrate comprising:
  (a) aliphatic short chain fatty acid;
  (b) a hydrotrope or solubilizer which is capable of solubilizing the fatty acid when the concentrate is diluted with a major amount of water; and
  (c) sufficient hydrotrope-compatible or solubilizer-compatible acid so that the use solution has a pH in the range of 2.0 to 5.0.

Another aspect of the present invention is a low foaming, aqueous antibacterial "use" solution which is particularly suited for "in-place" cleaning applications. The use solution comprises:
  (a) at least about 50 parts per million (ppm) to about 150 ppm short chain aliphatic fatty acid;
  (b) at least about 100 ppm hydrotrope or solubilizer for the fatty acid; and
  (c) sufficient hydrotrope-compatible acid so that the use solution has a pH in the range of 2.0 to 5.0.

As the term is used herein, "short chain fatty acid" is intended to mean fatty acids having from about 6 to 14 carbon atoms, preferably from about 8 to 12 carbon atoms. These fatty acids occasionally may be referred to herein as $C_6$–$C_{14}$ and $C_8$–$C_{12}$ fatty acids, respectively.

In yet a third aspect of the present invention there is described a fatty acid sanitizer or sanitizing composition as described above, the fatty acid component of which comprises a specified mixture of short chain fatty acids. This mixture of short chain fatty acids is the preferred fatty acid component of the present sanitizing composition and comprises 30% to 70% by weight fatty acid having from 6 to 9 carbon atoms (i.e., $C_6$–$C_9$), the remainder of the fatty acid component comprising short chain fatty acids (as defined herein) having longer aliphatic chains. Thus, the remainder of this preferred fatty acid component comprises $C_{10}$–$C_{14}$ carboxylic acids.

The present invention further contemplates methods of using the instant composition, such as the cleaning or sanitizing of "in-place" assemblies discussed above. This method comprises the steps of introducing the instant composition into the "in-place" system generally at ambient temperature, circulating the material through the system and optionally rinsing the system with potable water. Such applications generally utilize the advantageous low-foaming character of the present compositions. However, as will be discussed, high-foaming compositions are within the scope of the present invention and may be employed where foam is not problematic.

DETAILED DESCRIPTION OF THE INVENTION

The present invention is based upon the surprising and unexpected discovery that certain short chain aliphatic fatty acids exhibit enhanced antimicrobial activity, and in the environment described, can be used as a low-foaming sanitizing composition. Two discoveries prompted the present invention. First, it was found that at least with regard to organisms *Escherichia coli* (a gram negative microorganism) and *Staphylococcus aureus* (a gram positive microorganism) short chain fatty acids provided in 99.999% kill (5 $\log_{10}$ reduction). It is to be understood that under the conditions employed (i.e., pH generally in the range of 2.0 to 5.0), the short chain aliphatic, protonated parent acid (as opposed to the deprotonated carboxylate species or a fatty acid derivative, e.g., esters) was found to be the active component. This is unexpected because of the extensive discussions in the art of the biocidal activity of fatty acid derivatives, sometimes with little real concern with identifying the precise chemical species present.

The second discovery upon which a preferred aspect of the present invention is based is the fact that a combination of short chain fatty acids (in addition to the other components of the invention) provides enhanced antimicrobial activity. For example, it has been found that selecting a first short chain fatty acid from the group consisting of aliphatic fatty acids having from 6 to 9 carbon atoms and mixing this first short chain fatty acid with a second aliphatic fatty acid having from 10 to 14 carbon atoms and using this mixture of short chain fatty acids as the fatty acid component of the composition produces particularly enhanced antimicrobial activity. Without being bound to any theory, it is thought that the $C_6$ through $C_9$ aliphatic fatty acids tend to solubilize (i.e., to increase their aqueous solubility) the longer chain fatty acids which in turn provide better antimicrobial activity, particularly against gram positive organisms as well as enhanced foam control. Thus, a preferred fatty acid component consists essentially of about 30 to 70 weight percent $C_6$ to about $C_9$ fatty acid. The remainder of the fatty acid component being $C_{10}$ to $C_{14}$ aliphatic fatty acid.

The short chain fatty acids employed in the present invention may be structurally represented as follows:

$$R_1\text{—COOH} \hspace{4cm} (I)$$

wherein $R_1$ is an aliphatic hydrocarbon moiety having from about 5 to 13 carbon atoms (a $C_8$ fatty acid is generally represented structurally as $C_7$-COOH). $R_1$ may be saturated, unsaturated or aromatic, but is preferably saturated. $R_1$ may have substituents, e.g., —OH, or heteroatoms, e.g., —O— as in alkylether carboxylic acids, as long as neither its hydrophobicity nor the antimicrobial properties of the overall composition are significantly affected. ($R_1$ is preferably not unsubstituted). It should be recognized that "R", substituents or heteroatoms may change the overall acidity (i.e., pKa) of the fatty acids herein described. Such modification is within the contemplation of the present invention, provided the advantageous antimicrobial performance is maintained. Further, $R_1$ may be linear, branched or cyclic but is preferably linear because it has been shown that linear hydrocarbon residues tend to be more active than equivalent, branched isomers. Preferred hydrocarbon moieties (i.e., preferred $R_1$'s) include linear hydrocarbon aliphatic moieties having from 7 to 11 carbon atoms. It has been found that fatty acids within this narrower range of carbon atom content are particularly suited for "in-place" cleaning or sanitizing such as that employed in cleaning dairy farm pipelines and other milk handling equipment or in a dishwashing operation. Futhermore, this narrower range of fatty acids has been found to provide better antibacterial activity against both gram positive and gram negative microorganisms when a hydrotrope or coupler and requisite pH are employed.

As noted in passing above, —COOH is intended to exclude deprotonated species (i.e., salts) as well as fatty acid derivatives. These species simply would be present in insignificant concentrations under the conditions (particularly of pH) required herein.

The Hydrotrope or Solubilizer

The secondary necessary component of the present sanitizer composition is a surfactant hydrotrope, coupler or solubilizer for the short chain fatty acid. Hydrotropes or solubilizers for fatty acids are well known in the art to which this invention pertains. Functionally speaking, suitable solubilizers herein are non-toxic, surface active and retain the fatty acid in aqueous solution throughout the temperature range and concentration to which a concentrate or any "use" solution is exposed. (Even high-foaming hydrotropes, e.g., $C_{10}$, $C_{12}$ alkyl derivatives, may be employed where foam is permissible.) Perhaps the only limitation on the class of chemicals from which the solubilizer may be chosen is that nonionic surfactants are not preferred. It has been found that, while somewhat useful, nonionic surfactants with low critical micelle concentrations tend to detract from the biocidal activity of the short chain fatty acids and thus detract from the overall efficacy of the present composition. Representative classes of hydrotropes or solubilizers for the fatty acids which are preferred herein include anionic surfactants such as alkyl sulfates and alkane sulfonates, linear alkyl benzene or naphthalene sulfonates, alpha-olefin sulfonates, secondary alkane sulfonates, alkyl ether sulfates or sulfonates, alkyl phosphates, or phosphonates, dialkylsulfosuccinic acid esters, sugar esters (e.g., sorbitan esters) and $C_8$–$C_{10}$ alkyl glucosides.

One skilled in the art will readily appreciate that some of the above hydrotropes or couplers independently exhibit antibacterial activity at low pH. This, of course, adds to the efficacy of the present invention, but is not the primary criterion used in selecting an appropriate coupler. Since it is the presence of fatty acid in the protonated neutral state which provides biocidal activity herein, the coupler should be selected not for its independent antimicrobial activity but for its ability to provide effective interaction between the substantially insoluble fatty acids described herein and the microorganisms which the present compositions control.

Hydrotrope-Compatible Acids

As noted above, the present sanitizer composition requires the presence of a hydrotrope-compatible acid in sufficient concentration to rovide a pH in the range of about 2 to 5 (preferably about 2.0 to about 4.0 most preferably 2.5 to 3.5) when the concentrate is diluted to its use concentration. "Hydrotrope-compatible" herein is intended to mean that the acid employed should be compatible with the hydrotrope employed in terms of product stability and in terms of not causing degredation of the hydrotrope (e.g., hydrolysis). Further, the acid selected herein should have properties that are appropriate for the intended end use of the sanitizer composition. For example, when an alkyl sulfate hydrotrope (e.g., octyl or lauryl sulfate) is employed, a relatively weak, generally organic, acid such as citric acid, hydroxy acetic acid, fumaric acid, or maleic acid should be employed. Such acids are relatively weaker (i.e., less proton donating) than inorganic acids and while undoubtedly causing some degree of hydrolysis of alkyl sulfates, do not produce hydrolysis to the same extent. Citric acid is particularly desirable where higher pH and low toxicity are more desired as in sanitizing dishes and flatware. Additionally, citric acid was found to improve concentrate product stability under conditions where the concentrate is alternatively frozen and thawed. When the somewhat more stable (i.e., resistant to hydrolysis) alkyl sulfonates are employed as the hydrotrope, stronger hydrotrope-compatible acids such as phosphoric acid or sulfamic acid may be employed.

Phosphoric acid is a particularly advantageous acid for use in cleaning dairy pipelines because it tends to dissolve milk stone (calcium carbonate) which collects in dairy and creamery pipelines.

Optional Components

Other optional materials may be added to the composition either to restrict or enhance the formation of foam, to control hard water, or to further enhance the antimicrobial activity of the composition. For example, mono, di and tri alkyl phosphate esters may be added to the composition to suppress foam. Such phosphate esters would generally be produced from aliphatic linear alcohols, there being from 8 to 12 carbon atoms in the aliphatic portions of the alkyl phosphate esters. Coincidently, alkyl phosphate esters possess some antimicrobial activity in their own right under the conditions of the present invention. This antimicrobial activity also tends to add to the overall antimicrobial activity of the present compositions even though the phosphate esters may be added for other reasons. Furthermore, the addition of a small amount (so as not to restrict fatty acid activity) of nonionic surfactant would tend to reduce foam formation herein. Such materials tend to enhance performance of the other components of the composition, particularly in cold or soft water. A particularly useful nonionic surfactant for use as a defoamer herein is nonylphenol having an average of 12 moles of ethylene oxide condensed thereon, it being encapped with a hydrophobic portion comprising an average of 30 moles of propylene oxide.

Chelating agents can be added to the composition to enhance biological activity and cleaning performance. For example, one-hydroxy ethylidene-1, one-di-phosphonic acid commercially available from the Monsanto Company under the trade designation "Dequest" has been found to assist in the disruption of cell structure of the polysaccharide-divalent metal ion complex thought to exist in gram negative microorganisms. Citric acid is also found to interrupt such gram negative microorganism complexes. Other materials which are sufficiently stable at the low pH contemplated by the present composition may be added to the composition to impart desirable qualities depending upon the intended ultimate use. Chelating agents optionally can be added to the present composition to control (i.e., to sequester) hardness ions such as calcium and magnesium. In this manner both detergency and sanitization capability can be enhanced.

Other materials can be added to the concentrate (and thus ultimately to the use solution) to change its color or odor, to adjust its viscosity, to enhance its thermal (i.e., freeze-thaw) stability or to provide other qualities which tend to make it more marketable. For example, isopropanol, ethanol or generally-recognized-as-safe (GRAS) flavoring agents of the ethyl fatty acid esters, in small amounts (e.g., approximately 0.1 to 0.2%) can be added to the composition to reduce viscosity and to reduce fatty acid odor. Unfortunately, the addition of alcohols under the strongly acidic conditions of the concentrate tends to induce esterification. The formation of less active esters reduces the concentration of fatty acids and thus reduces composition activity. Thus, if an alcohol solvent is to be used, there tends to be trade off between reduction in viscosity and reduction in antibacterial activity.

The Method

As noted above, the particular preferred utility of the present composition is the cleaning or sanitizing of a substantially fixed "in-place" processing facilities such as are utilized in the food industry, dairy industry and in the brewery industry. Generally, the actual cleaning of the "in-place" system (i.e., removal of unwanted offal therein) is accomplished with a different material (e.g., glassware detergent) which is introduced with heated water. After the cleaning step, the instant sanitizing composition would be introduced into the system (at a "use" solution concentration) in unheated, ambient temperature water. The present sanitizing composition is found to remain in solution in cold (e.g., 40° F./4° C.) water and heated water (e.g., 140° F./60° C.). Although it is not normally necessary to heat the aqueous use solution of the present composition, under some circumstances heating may be desirable to further enhance its antimicrobial activity. After introduction of the present sanitizing use solution, the solution is circulated throughout the system to sanitize (i.e., to kill undesirable microorganisms). After the system has been sanitized by means of the present composition, the use solution is drained from the system. Upon completion of the sanitizing step, the system optionally may be rinsed with other materials including potable water. As the term "sanitizing" is used in the method of the instant invention, it means reduction of undesirable microorganisms by about 5 powers of 10 (i.e., 5 orders of magnitude). It is to be emphasized that the instant compositions provide cleaning as well as sanitizing performance even though their primary utility is in sanitizing.

A Typical Concentrate Composition

The present invention contemplates a concentrate which is diluted to a "use" concentration prior to its utilization as a sanitizer. Primarily for reasons of economics, the concentrate would normally be marketed and the end user would dilute the concentrate with water to a use concentration. Typical composition weight percentages for the concentrate are indicated in Table I.

TABLE I

Typical Fatty Acid Sanitizer Compositions

| Component | Typical range percent by weight |
|---|---|
| Short chain fatty acids | 3–12 |
| Hydrotrope or coupler | 10–20 |
| Acid | 20–50 |
| Solvent or Defoamer | 0–2 |
| Water | Balance |

The level of active components in the concentrate composition is dependent upon the intended dilution factor and desired acidity in the use solution. Fatty acids are generally readily dissolved in the coupler or hydrotrope, which is to be premixed with the desired amount of acid. The resulting concentrate is easily diluted with water to provide the use solution. Generally, a dilution of 1 fluid ounce to 5 gallons (i.e., dilution of 1 to 640 by volume) or to 7 gallons (i.e., 1 to 900 dilution) of water can be obtained with 8% or 10% fatty acids in the concentrate, respectively (see examples). Higher use dilution can be employed if elevated use temperature (>20° C.) or extended exposure time (>30° seconds) are also employed. Higher use temperatures or longer exposure times would be common in many practical situations such as dishwashing or laundry.

The "Use" Composition

In its intended end use, the concentrate is diluted with a major amount of water and used for purposes of sanitation or sanitizing. The typical concentrate composition described above is diluted with available tap water to a formulation of approximately one ounce (28.3 grams) concentrate to five gallons (18.9 liters) water (1 to 640 by volume). Typical use solutions are outlined in Table II.

TABLE II

Typical "Use" Solution Concentrations

| Component | Typical range, ppm | |
|---|---|---|
| | 1 oz./5 gal. | 1 oz./7 gal. |
| Short chain fatty acid | 50 to 150 | 50 to 150 |
| Hydrotrope or coupler | 150 to 300 | 150 to 250 |
| Acid | 500 to 1000 | 200 to 500 |
| Solvent or defoamer | 0 to 40 | 0 to 40 |
| Water | balance | balance |

While a dilution of the concentrate using a ratio of one ounce to five gallons is particularly preferred herein, as indicated in Table II and III (below), less concentrated use solutions may be employed.

Antimicrobial Efficacy Examined

While not being bound to any theory herein, we have found that the antimicrobial efficacy of the composition described herein is dependent upon pH, and the temperature of use conditions, the hydrophobicity and pK of bacterial cell surfaces, and the structure and chain length of fatty acids.

Changes in the pH of the use solution can markedly affect the ionic characteristics of the polar region of the cell surface and the extent of dissociation of the fatty acids. For example, decreasing pH can increase the hydrophobic properties of fatty acids (less carboxylate form) and phospholipids (less phosphate form) of cell membrane. This tends to improve the permeability of phospholipid cell surfaces to lipophilic molecules such as short chain fatty acid, fatty alcohol or alkyl phosphate esters. The effect of lowering the pH on the cell proteins can be to increase the number of positive charges which attract and adsorb anionic surfactants such as n-alkane sulfonates, LAS, alkyl sulfate, etc. Thus, for certain microorganisms, lowering the pH tends to enhance cell membrane permeability of lipophilic molecules.

For different microorganisms, different changes in ionic character or hydrophobicity with pH change is probably due to the different pK values of cell surface (see Molecular Aspects of Biological Surfaces, A. M. James, *Chem. Soc. Review*, 389 (1979). With the same concentration of $C_8$ and $C_{10}$ fatty acid and coupler, the sanitizers retain their activity from pH 2 up to pH 3.2 for both *E. coli* (pK=2.9) and *S. aureus* (pK approximately 3.5). However, they continue to remain active against *S. aureus* up to pH=4.3, just below the dissociation constant of fatty acids (pKa approximately 4.5 to 5). An increase in temperature will also increase the optimum pH to 4 for both *E. coli* and *S. aureus* (Table III).

Effective contact between fatty acid or surfactant with microorganism is believed to be the most important factor in determining the efficiency of an antimicrobial agent. However, the structure and chain length of the hydrophobic group ($R_1$) determines the antimicrobial effectiveness against specific classes or organisms. It is generally recognized that an increase in the length of $R_1$ reinforces the binding of anionic or cationic surfactants to the hydrophobic region of bacterial membrane. For the short chain fatty acids or lipophilic molecules, the increasing chain length may improve the permeability of the less polar molecular through the phospholipid membrane. Our results indicate the gram negative *E. coli* is more affected by the linear $C_8$ or $C_9$ fatty acids or by $C_8$ sulfonate, sulfate and phosphate surfactants at low pH while the gram positive *S. aureus* is more affected by the $C_{10}$ or $C_{12}$ homologs. The effective chain length or the hydrophobicity of $R_1$ is also affected by the presence of substituents or unsaturation. For a given chain length, the short chain linear and saturated fatty acid or n-alkane sulfonate surfactant is more effective than the branched isomer or unsaturated analogs.

Improving the hydrophobicity of fatty acid by introducing polar functional group, such as hydroxy or sulfonate also reduces its antimicrobial activity. The use of highly effective and safe lipophilic molecules of fatty acids, fatty alcohols or alkyl phosphate esters suggests that the penetration of these molecules through the lipid membrane may be the possible antimicrobial action. Due to the different hydrophobicities of various organisms, the mixed chain lengths which act effectively against broad spectrum of organisms are greatly preferred in the sanitizing compositions as shown in the examples. In addition, the $C_{10}$ or $C_{12}$ fatty acid also provides excellent foam control in the use conditions where low foam is desired.

The attached examples are intended to illustrate the above invention and should not be construed so as to narrow its scope. One skilled in the art will readily recognize that these examples suggest many other ways in which the present invention could be practiced.

EXAMPLE 1

A mixture of short chain fatty acids commercially available from the Emery Corporation under the designation EMERY 6358 (food grade) is employed to produce a sanitizing composition of the present invention. The "6358" acid mixture comprises approximately 60% caprylic acid ($C_8$), the remainder being capric acid ($C_{10}$). This material available from Emery Corporation is found to be substantially equivalent to a material available from Procter & Gamble Corporation having the trade designation "C-810". The fatty acid mixture was combined with a premixture of n-octanesulfonates anionic coupler (comprising approximately 80% of the sodium salt of 1-octane sulfonate, the remainder being 1,2-octanedisulfonate disodium salt.) The octane sulfonates are made by the reaction of 1-octene with sodium bisulfite using a free radical initiator (e.g., t-butyl perbenzoate) and a mixture of citric acid and phosphoric (75%). The final composition of this material was as follows:

| | Wt. % |
|---|---|
| Caprylic acid ($C_8$) | 4.8% |
| Capric acid ($C_{10}$) | 3.2% |
| n-Octanesulfonates | 12.0% |
| Citric acid | 22.5% |
| $H_3PO_4$ (75%) | 30.0% |

-continued

| | Wt. % |
|---|---|
| Water | Balance |

A one ounce to five gallon dilution of this composition provided a pH of 2.5 to 2.7.

EXAMPLE 2

A second material of the present invention was prepared as outlined in Example 1, the difference being that the concentration of fatty acids was increased from a total of 8 weight percent to a total of 10 weight percent. In addition, the n-octansulfonates coupler concentration was increased to 15 weight percent, the citric acid concentration being increased to 25 weight percent while the concentration of phosphoric acid was decreased to 25 weight percent. A one ounce/seven gallon dilution in water provided a pH of 3.0 to 3.3.

EXAMPLE 3

The composition of the present invention was prepared in accordance with the steps outlined in Example 1, the difference being that a mixture of pelargonic acid ($C_9$) and capric acid ($C_{10}$) is used. In addition, a chelating agent was added. The composition of this material is as follows:

| | Wt. % |
|---|---|
| Pelargonic acid ($C_9$) | 6.0% |
| Capric acid | 4.0% |
| n-Octanesulfonates | 15.0% |
| Citric acid | 30.0% |
| Dequest 2010 (60%) | 20.0% |
| Water | Balance |

Pelargonic acid is a synthetic fatty acid, previously discussed $C_8$ and $C_{10}$ materials being derived from natural vegetable sources. This product is commercially available from the Emery Corporation under the trade designation "1202". Capric acid is also available commercially from the Emery Company under the trade designation "EMERY 659". The material sold by the Emery Company under the trade designation "659" is approximately 97% $C_{10}$ fatty acid, approximately 2% $C_{12}$ fatty acid and about 1% $C_8$ fatty acid.

EXAMPLE 4

In accordance with the procedure outlined in Example 1, the composition of the present invention was prepared using an octyl sulfate coupler. The composition of this material is as follows:

| | Wt. % |
|---|---|
| Pelargonic acid | 6.0% |
| Capric acid | 4.0% |
| Octyl sulfate | 15.0% |
| Citric acid | 40.0% |
| Water | Balance |

The octyl sulfate used in this example is commercially available from the DuPont Company, the trade designation "DUPONOL SP".

EXAMPLE 5

The following composition was prepared according to the procedure of Example 1. This composition is a high foaming material having but a 1 ounce to 2 gallon use dilution at 3% fatty acid in the concentrate.

| | Wt % |
|---|---|
| Emery 6358 short chain fatty acid | 3.0 |
| Hostapur SAS* coupler | 12.0 |
| Citric acid | 35.0 |
| Water | Balance |

*Hostapur SAS is commercial secondary n-alkane sulfonates ($C_{13}$-$C_{18}$) available from American Hoechest Corp.

EXAMPLE 6

The materials in Examples 1, 2, 3, 4 and 5 were tested for various properties including antimicrobial activity as outlined in Table III.

TABLE III

| Example | (oz/gal) Dilution | pH[a] | Concentration (ppm) Fatty acid | Concentration (ppm) Coupler | Percent kill[b] E. coli | Percent kill[b] S. aureus | Dynamic foam[c] Ht (ml)/collapse time (sec) |
|---|---|---|---|---|---|---|---|
| 1 | 1/5 | 2.7 | 150-155 | 225-235 | 99.999 | 99.999 | 275 (11) |
|  | 1/6 | 2.9 | 125-130 | 185-195 | 99.999 | 99.999 | 250 (8) |
| 2 | 1/7 | 3.1 | 140-145 | 210-220 | 99.999 | 99.999 | 250 (9) |
|  | 1/8 | 3.3 | 120-130 | 185-195 | 99.999 | 99.999 | 225 (8) |
| 3 | 1/8 | 3.3 | 120-130 | 185-195 | 99.999 | 99.999 | 270 (7) |
|  | 1/10 | 3.6 | 100 | 150 | 99.999 | 99.999 (at 40° C.) | low |
|  | 1/13 | 4.0 | 75 | 115 | 99.999 | 99.999 (at 40° C.) | low |
|  | 1/20 | 4.0 | 50 | 75 | 99.999 | 99.999 (at 40° C., 180 sec exposure) | low |
| 4 | 1/7 | 3.3 | 140-145 | 210-220 | 99.999 | 99.999 | 300 (10) |
| 5 | 1/2 |  | 120 | 480 | 99.999 | 99.999 | 750 ml (5 min.) |
| Control |  | 2.7 | 0 | 225-235[d] | ~90 | ~90 | 400 (19) |

NOTES:
[a] pH were measured using an "Orion" pH meter in 500 ppm synthetic hard water
[b] antimicrobial tests were conducted according to the method of A.O.A.C. "Germicidal and Detergent Sanitizer Test", 10th Edition, p. 87 (1965) in 500 ppm synthetic hard water (500 ppm calcium carbonate added), at 20° C. and 30 seconds exposure time, with 75 to 125 × $10^6$ organisms/ml.
[c] 15 second dynamic foam volume of 300 ml use solution (500 ppm synthetic hard water) measured at 25° C. and 2 liters/min. air flow rate.
[d] for comparison, an n-octanesulfonates coupler was mixed with a phosphate acid/citric acid mixture.

Table III clearly indicates the antimicrobial efficacy of materials of the present invention relative to a "control" in which the short chain fatty acid was omitted. As noted above, n-octanesulfonate couplers do exhibit some antibacterial behavior, particularly at low pH. This is borne out in Table III wherein approximately 90% reduction in population of the gram positive and gram negative E. coli and S. aureus microorganisms was achieved. A 90% kill might be acceptable for some applications for most "in-place" sanitizing applications, a 90% reduction in the microorganism population would be considered a failure.

The second column of Table III indicates that the concentrate of the present invention may be diluted from about 1 oz. to 2 gallon up to 1 oz. to 20 gallons. As the four dilutions in Example 3 indicate, with higher dilutions (e.g., 1/8, 1/10, 1/13, 1/20), similar rates of kill may be obtained at 40° C. and with a longer exposure period. These conditions are roughly comparable to those obtained in low temperature dishwashing operation which employs a fairly standard three minute washing cycle.

The composition from Example 5 illustrates that the advantageous sanitizing properties of the present invention may be obtained even though a high-foaming hydrotrope or coupler (in this case, a secondary n-alkane sulfonate) is employed. Such a high-foaming coupler would not normally be useful for "in-place" sanitizing applications.

Various modifications and alterations of the invention will become apparent to those skilled in the art without departing from the scope and spirit of the invention. It should be understood that this invention is not to be limited to the illustrative embodiments and examples set forth herein.

What is claimed is:

1. A concentrate composition which is capable of being diluted with a major amount of water to form an antimicrobial sanitizing use solution, the concentrate composition comprising:
    (a) an aliphatic, short chain fatty acid;
    (b) an effective amount of an ionic hydrotrope-solubilizer which is capable of solubilizing the aliphatic, short chain fatty acid when the concentrate is diluted with water; and
    (c) sufficient hydrotrope-solubilizer-compatible acid so that the antimicrobial sanitizing use solution has a pH in the range of about 2.0 to 5.0.

2. The composition of claim 1 wherein the aliphatic, short chain fatty acid has about 6 to 14 carbon atoms.

3. The composition of claim 1 wherein the aliphatic, short chain fatty acid has 8 to 12 carbon atoms.

4. The composition of claim 1 wherein the aliphatic, short chain fatty acid is a linear, saturated fatty acid having about 6 to 14 carbon atoms.

5. The composition of claim 1 wherein the linear, saturated fatty acid has about 8 to 12 carbon atoms.

6. The composition of claim 1 that further comprises alkyl phosphate ester.

7. The composition of claim 1 wherein the alkyl phosphate ester is selected from a group consisting of mono, di, tri alkyl phosphate esters or mixtures of any combination of mono, di and tri alkyl phosphate esters.

8. The composition of claim 1 which further comprises a nonionic surfactant foam suppressant.

9. The composition of claim 8 wherein the nonionic surfactant foam suppressant is nonylphenol-polyethoxylate polypropoxylate, there being respectively an average of 12 moles of ethylene oxide and an average of 30 moles of propylene oxide.

10. The composition of claim 1 wherein the aliphatic, short chain fatty acid component comprises a mixture of aliphatic short chain fatty acid, the fatty acids having about 6 to 14 carbon atoms.

11. The composition of claim 10 wherein the mixture of aliphatic, short chain fatty acids comprises 30% to 70% by weight of a fatty acid having about 6 to 9 carbon atoms, the remainder comprising fatty acid having about 10 to 14 carbon atoms.

12. The composition of claim 1 wherein the aliphatic, short chain fatty acid component is a mixture of short chain fatty acids comprising from about 30 to 70% by weight fatty acid having about 6 to 9 carbon atoms, the remainder being fatty acids having about 10 to 14 carbon atoms.

13. The composition of claim 12 which further comprises alkyl phosphate ester.

14. The concentrate which is capable of being diluted with a major amount of water to form a low-foaming, antimicrobial sanitizing solution, the concentrate comprising:
    (a) a fatty acid of the structure $R_1$-COOH $R_1$ being a linear, saturated, branched or unbranched hydrocarbon chain having about 7 to 13 carbon atoms;
    (b) an effective amount of an ionic hydrotrope-stabilizer which is capable of solubilizing the fatty acid when the concentrate is diluted with water; and
    (c) sufficient hydrotrope-sanitizer compatible acid so that the antimicrobial sanitizer use solution has a pH in the range of about 2.0 to 5.0.

15. The composition of claim 14 wherein $R_1$ comprises a mixture of hydrocarbon chains including 30 to 70 weight percent chains having about 5 to 8 carbon atoms, the remainder of $R_1$'s having about 9 to 13 carbon atoms.

16. The composition of claim 15 wherein the hydrotrope-solubilizer is n-octanesulfonates.

17. The composition of claim 15 wherein the hydrotrope-sanitizer compatible acid is a mixture of phosphoric acid and citric acid.

18. A low foaming, aqueous, antimicrobial, sanitizing composition which comprises:
    (a) at least about 50 parts per million (ppm) short chain aliphatic fatty acid having about 6 to 14 carbon atoms;
    (b) at least about 100 ppm of a hydrotrope-solubilizer for the fatty acid; and
    (c) sufficient hydrotrope-solubilizer-compatible acid so that the composition has a pH in the range of 2.0 to 5.0.

19. The composition of claim 18 wherein the short chain aliphatic fatty acid is linear, saturated, and comprises a mixture of about 30 to about 70 percent by weight fatty acids having 6 to 9 carbon atoms, the remainder comprising fatty acids having 10 to 14 carbon atoms.

20. The composition of claim 18 wherein the hydrotrope-solubilizer is n-octanesulfonates.

21. The composition of claim 18 wherein the hydrotrope-solubilizer-compatible acid is a mixture of phosphoric acid and citric acid.

22. A method of sanitizing substantially fixed "in-place" process facilitates comprising:
    introducing into the process facilitates the composition of claim 18 at a temperature in the range of about 40° F. (4° C.) to 140° F. (60° C.);
    circulating the composition through the process facilitates for a time sufficient to sanitize the process facilitates; and
    draining the composition .

23. The composition of claim 22 wherein the processing facilities comprise a milk line dairy.

24. The composition of claim 22 wherein the process facilities comprise a continuous brewing system.

25. The composition of claim 22 wherein the composition of claim 18 is circulated through the system to the composition for 30 seconds or less.

26. The method of claim 22 wherein after the composition is drained from the process facilities the process facilities are rinsed with potable water.

* * * * *

UNITED STATES PATENT AND TRADEMARK OFFICE
CERTIFICATE OF CORRECTION

PATENT NO. : B1 4,404,040
DATED : July 16, 1991
INVENTOR(S) : Yueh Wang

It is certified that error appears in the above-identified patent and that said Letters Patent is hereby corrected as shown below:

At column 3, line 47, please delete "sand" and instead insert --said--.

At column 4, line 18, please delete "composition" and instead insert --concentrate--.

Signed and Sealed this

Eleventh Day of February, 1992

Attest:

HARRY F. MANBECK, JR.

*Attesting Officer*  *Commissioner of Patents and Trademarks*

REEXAMINATION CERTIFICATE (1510th)

United States Patent [19]

Wang

[11] B1 4,404,040

[45] Certificate Issued Jul. 16, 1991

[54] SHORT CHAIN FATTY ACID SANITIZING COMPOSITIONS AND METHODS

[75] Inventor: Yueh Wang, Apple Valley, Minn.

[73] Assignee: Economics Laboratory, Inc., St. Paul, Minn.

Reexamination Request:
No. 90/000,886, Oct. 11, 1985

Reexamination Certificate for:
Patent No.: 4,404,040
Issued: Sep. 13, 1983
Appl. No.: 279,442
Filed: Jul. 1, 1981

[51] Int. Cl.$^5$ .......... A61L 2/00; B08B 9/00; C11D 3/48; C11D 7/08
[52] U.S. Cl. .................. 134/22.14; 134/30; 252/106; 252/108; 252/135; 252/142; 252/174.16; 252/DIG. 14; 252/DIG. 17; 252/363.5; 422/28
[58] Field of Search ............ 134/22.14, 30; 252/106, 252/108, 135, 142, 174.16, 363.5, DIG. 14, DIG. 17; 422/28

[56] References Cited

U.S. PATENT DOCUMENTS

| | | | |
|---|---|---|---|
| 2,668,150 | 2/1954 | Luvisi | 252/321 |
| 3,042,621 | 7/1962 | Kirschenbauer | 252/99 |
| 3,150,096 | 9/1964 | Schmidt et al. | 252/106 |
| 3,218,260 | 11/1965 | Lewandowski | 252/142 |
| 3,438,906 | 4/1969 | Duvall | 252/106 |
| 3,525,696 | 8/1970 | Schmidt et al. | 252/106 |
| 3,560,390 | 2/1971 | Gaines | 252/107 |
| 3,650,965 | 3/1972 | Cantor et al. | 252/106 |
| 3,915,633 | 10/1975 | Ramachanoran | 8/137 |
| 4,164,477 | 8/1979 | Whitley | 252/99 |
| 4,404,040 | 9/1983 | Wang | 134/22.14 |

FOREIGN PATENT DOCUMENTS

| | | | |
|---|---|---|---|
| 553057 | 2/1959 | Canada . | |
| 657564 | 2/1963 | Canada | 134/6 |
| 1018854 | 10/1977 | Canada . | |
| 2401062 | 7/1974 | Fed. Rep. of Germany | 252/142 |
| 2310246 | 9/1974 | Fed. Rep. of Germany . | |

OTHER PUBLICATIONS

Keeney, E. L., Sodium Caprylate, *A New and Effective Treatment for Moniliasis of the Skin,* 78 Bull. Johns Hopkins U. (1946) pp. 333–339.

Morrison, Robert T. et al., *Organic Chemistry* (1959) pp. 438–439.

Canas-Rodriguez, A. et al., *The Identification of the Antimicrobial Factors of the Stomach Contents of Sucking Rabbits,* 100 Biochem. J. (1966) pp. 79–82.

Fay, J. P. et al., *The Inhibitory Action of Fatty Acids on the Growth of Esterchia coli,* 91 J. General Microbiology (1975) pp. 233–240.

Journal of Food Protection, "Food–Grade Chemicals for Use in Designing Food Preservative Systems", Jon J. Kabara, vol. 44, Aug. 1981, pp. 633–647.

*Primary Examiner*—Michael R. Lusignan

[57] ABSTRACT

Sanitizing concentrate and "use" compositions comprising aliphatic, short chain fatty acid (i.e., $C_6$–$C_{14}$ fatty acid), hydrotrope or solubilizer for the fatty acid, hydrotope-compatible acid so that the concentrate, when diluted with a major amount of water provides a use solution having a pH in the range of 2.0 to 5.0. Sanitizing of substantially fixed, "in-place" processing lines in dairies, breweries and other food processing operations is a particular utility of this invention.

## REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 25, 26 are cancelled.

Claims 1, 5, 10, 14, 15, 16, 18, 20, 22, 23, 24 are determined to be patentable as amended.

Claims 2-4, 6-9, 11-13, 17, 19, 21, dependent on an amended claim, are determined to be patentable.

New claims 27-46 are added and determined to be patentable.

1. A concentrate composition which is capable of being diluted with a major amount of water to form an antimicrobial sanitizing use solution, the concentrate composition [comprising] *consisting essentially of, in* an aqueous base:
   (a) *an effective amount of* an aliphatic, *saturated* short chain fatty acid;
   (b) an effective amount of an [ionic] *anionic* hydrotrope-solubilizer which is capable of solubilizing the aliphatic, short chain fatty acid when the concentrate is diluted with water; and
   (c) sufficient hydrotrope-solubilizer-compatible acid so that the antimicrobial sanitizing use solution has a pH in the range of about 2.0 to 5.0;
   *wherein the concentrate can be diluted to form a sanitizing use solution having at least about 50 parts of the fatty acid, about 200 parts hydrotrope-solubilizer compatible acid, and about 100 parts hydrotrope-solubilizer each per million parts of the use solution wherein said use solution produces less than 275 millimeters of foam at 25° C. after 15 seconds of air flow at 2 liters of air per minute.*

5. The composition of claim 1 wherein the *aliphatic, short chain fatty acid is a* linear, saturated fatty acid [has] *having* about 8 to 12 carbon atoms.

10. The composition of claim 1 wherein the aliphatic, short chain fatty acid component comprises a mixture of aliphatic short chain fatty acid, the fatty acids having about 6 to 14 carbon atoms *and wherein the anionic hydrotrope solubilizer comprises an alkyl sulfonate or an alkyl naphthalene sulfonate.*

14. [The] *A* concentrate which is capable of being diluted with a major amount of water to form a low-foaming, antimicrobial sanitizing solution, the concentrate [comprising] *consisting essentially of, in an aqueous base:*
   (a) *about 3 to 12 wt-% of* a fatty acid of the structure R₁—COOH, R₁ being a linear, saturated, branched or unbranched hydrocarbon chain having about [7 to 13] *6 to 14* carbon atoms;
   (b) [an effective amount] *about 8 to 20 wt-% of an* [ionic hydrotrope-stabilizer] *anionic hydrotrope-solubilizer comprising an alkyl sulfate, an alkyl sulfonate, an aromatic sulfate, or an aromatic sulfonate* which is capable of solubilizing the fatty acid when the concentrate is diluted with water; and
   (c) [sufficient hydrotrope-sanitizer] *about 20 to 50 wt-% of a hydrotrope-solubilizer* compatible acid so that the antimicrobial sanitizer use solution has a pH in the range of about 2.0 to 5.0;
   *wherein the concentrate can be diluted to form a sanitizing use solution having about 50 to 150 parts of the fatty acid, 100 to 300 parts hydrotrope solubilizer and 200 to 1,000 parts of compatible acid each per million parts of the use solution wherein said use solution produces less than 275 milliliters of foam at 25° C. after 15 seconds of air flow at 2 liters of air per minute.*

15. The composition of claim 14 wherein R₁ comprises a mixture of hydrocarbon chains including 30 to 70 weight percent chains having about [5 to 8] *6 to 9* carbon atoms, the remainder of R₁'s having about [9 to 13] *10 to 14* carbon atoms.

16. The composition of claim 15 wherein the hydrotrope-solubilizer is [n-octanesulfonates] *an n-octanesulfonate or an alkyl naphthalene sulfonate.*

18. A low foaming, *single-phase* aqueous, antimicrobial, sanitizing composition which [comprises] *consists essentially of, in an aqueous base:*
   (a) at least about 50 parts per million (ppm) short chain aliphatic *saturated* fatty acid having about 6 to 14 carbon atoms;
   (b) at least about 100 ppm of [a] *an anionic* hydrotrope-solubilizer for the fatty acid; and
   (c) sufficient hydrotrope-solubilizer-compatible acid so that the composition has pH in the range of 2.0 to 5.0;
   *wherein said sanitizing composition produces less than 275 milliliters of foam at 25° C. after 15 seconds of air flow at 2 liters of air per minute.*

20. The composition of claim 18 wherein the hydrotrope-solubilizer is n-octanesulfonates *or an alkyl naphthalene sulfonate.*

22. A method of sanitizing substantially fixed "in-place" process [facilitates] *facilities* comprising:
   introducing into the process [facilitates] *facilities* the composition of claim 18 at a temperature in the range of about 40° F. (4° C.) to 140° F. (60° C.);
   circulating the composition through the process [facilitates] *facilities* for a time sufficient to sanitize the process [facilitates] *facilities*; and draining the composition.

23. [The composition of claim 22] *The method of claim 22* wherein the processing facilities comprise a [milk line] *dairy*.

24. [The composition of claim 22] *The method of claim 22* wherein the process facilities comprise a continuous brewing system.

*27. A concentrate composition suitable for sanitizing surfaces which is capable of being diluted with a major amount of water to form an antimicrobial sanitizing use solution, the concentrate composition consisting essentially of:*
   *(a) about 3-12% of a mixture of a C₆₋₉ saturated short chain fatty acid and a C₁₀₋₁₂ saturated short chain fatty acid;*
   *(b) about 8 to 20 wt-% of an anionic hydrotrope-solubilizer which is capable of solubilizing the aliphatic short chain fatty acid when the concentrate is diluted with water;*

(c) about 20 to 50 wt-% of a hydrotrope-solubilizer-compatible acid sufficient to produce a pH in the range of about 2 to 5 in the antimicrobial sanitizing use solution; and (d) water;

wherein said use solution produces less than 275 milliliters of foam at 25° C. after 15 seconds of air flow at 2 liters of air per minute.

28. The concentrate composition of claim 27 wherein the hydrotrope-solubilizer comprises an n-alkylsulfonate or an alkyl naphthalene sulfonate.

29. The concentrate composition of claim 28 wherein the hydrotrope-solubilizer-compatible acid comprises citric acid, phosphoric acid, or mixtures thereof.

30. A low-foaming, aqueous, antimicrobial, single-phase sanitizing composition which consists essentially of:

(a) about 50–150 parts per million of a mixture of at least one $C_{6-9}$ saturated fatty acid and at least one $C_{10-12}$ saturated fatty acid;

(b) about 100 to 300 parts per million of an anionic hydrotrope-solubilizer for the fatty acid;

(c) about 200–1,000 parts per million of a hydrotrope-solubilizer-compatible acid; and (d) water;

wherein the pH of the sanitizing composition is in the range of 2 to 5 wherein said sanitizing composition produces less than 275 milliliters of dynamic foam at 25° C. after 15 seconds of air flow at 2 liters of air per minute.

31. The concentrate composition of claim 30 wherein the anionic hydrotrope-solubilizer comprises an n-alkylsulfonate.

32. The concentrate composition of claim 31 wherein the hydrotrope-solubilizer-compatible acid comprises citric acid, phosphoric acid, or mixtures thereof.

33. A low-foaming, aqueous antimicrobial single-phase sanitizing composition which consists essentially of:

(a) about 8 to 12 wt-% of a mixture of octanoic acid decanoic fatty acids;

(b) about 10 to 12 wt-% of sodium octyl sulfonate;

(c) about 20 to 50 wt-% phosphoric acid;

(d) about 20 to 40 wt-% citric acid;

(e) 0 to 0.2 wt-% isopropanol; and (f) water, wherein sand sanitizing composition produces less than 275 milliliters of dynamic foam at 25° C. after 15 seconds of air flow at 2 liters of air per minute.

34. A low-foaming, aqueous antimicrobial sanitizing single-phase composition comprises a dilute solution prepared by contacting about 1 oz. of the composition of claim 33 with from about 2 to 20 gallons of water.

35. A concentrate composition which is capable of being diluted with a major amount of water to form an antimicrobial sanitizing use solution, the concentrate composition consisting essentially of, in an aqueous base:

(a) about 3 to 12 wt-% of an aliphatic, saturated short chain fatty acid;

(b) about 8 to 20 wt-% of an anionic hydrotrope-solubilizer, for the fatty acid, comprising an alkyl sulfonate, an aromatic sulfonate, or mixtures thereof;

(c) sufficient hydrotrope-solubilizer-compatible acid so that the antimicrobial sanitizing use solution has a pH in the range of about 2.0 to 5.0;

wherein the concentrate can be diluted to form a sanitizing use solution having at least about 50 parts of the fatty acid, about 200 parts hydrotrope-solubilizer compatible acid, and about 100 parts hydrotrope-solubilizer each per million parts of the use solution wherein said sanitizing composition produces less than 275 milliliters of dynamic foam at 25° C. after 15 seconds of air flow at 2 liters of air per minute.

36. The composition of claim 35 wherein the aliphatic, short chain fatty acid has 8 to 12 carbon atoms.

37. The composition of claim 35 wherein the aliphatic, short chain fatty acid component comprises a mixture of aliphatic short chain fatty acids, the fatty acids having about 6 to 14 carbon atoms.

38. The composition of claim 35 wherein the hydrotrope-solubilizer compatible acid comprises citric acid, phosphoric acid, or mixture thereof.

39. The concentrate of claim 35 wherein the anionic hydrotrope-solubilizer comprises an alkyl sulfonate, an alkyl naphthalene sulfonate, or mixtures thereof.

40. A low-foaming, single-phase aqueous antimicrobial, sanitizing composition which comprises, in an aqueous base:

(a) at least about 50 parts per million (ppm) of a short chain aliphatic saturated fatty acid having about 6 to 14 carbon atoms;

(b) at least about 100 (ppm) of an anionic hydrotrope-solubilizer composition, which is capable of solubilizing a fatty acid, an alkyl sulfonate, an aromatic sulfonate, or mixtures thereof; and (c) sufficient hydrotrope-solubilizer compatible acid so that the composition has a pH in the range of 2.0 to 5.0, wherein said composition has less than 275 milliliters of foam at 25° C. after 15 seconds of air flow through 300 milliliters of the solution measured at 2 liters per minute.

41. The composition of claim 40 wherein the short chain aliphatic fatty acid is linear, saturated, and comprises a mixture of about 30 to about 70 percent by weight fatty acids having 6 to 9 carbon atoms, the remainder comprising fatty acids having 10 to 14 carbon atoms.

42. The composition of claim 40 wherein the hydrotrope-solubilizer is an n-octanesulfonate.

43. The composition of claim 40 wherein the hydrotrope-solubilizer-compatible acid is a mixture of phosphoric acid and citric acid.

44. A method of sanitizing substantially fixed "in-place" process facilities comprising:

(a) introducing into the process facilities the composition of claim 40 at a temperature in the range of about 40° F. (4° C.) to 140° F. (60° C.);

(b) circulating the composition through the process facilities for a time sufficient to sanitize the process facilities; and (c) draining the composition.

45. The method of claim 44 wherein the processing facilities comprise a dairy.

46. The method of claim 44 wherein the process facilities comprise a brewing system.

* * * * *